United States Patent [19]

Davis et al.

[11] Patent Number: 4,504,295

[45] Date of Patent: Mar. 12, 1985

[54] NITROGEN REJECTION FROM NATURAL GAS INTEGRATED WITH NGL RECOVERY

[75] Inventors: Ruth A. Davis, Whitehall; Donn M. Herron, Trexlertown; James W. Pervier, West Chester; Harvey L. Vines, Emmaus, all of Pa.

[73] Assignee: Air Products and Chemicals, Inc., Allentown, Pa.

[21] Appl. No.: 499,954

[22] Filed: Jun. 1, 1983

[51] Int. Cl.³ .................................. F25J 3/02
[52] U.S. Cl. ........................................ 62/30; 62/31; 62/33; 62/34; 62/39; 62/40
[58] Field of Search ................ 62/40, 38, 39, 9, 11, 62/23-31, 32-34, 42, 43; 203/DIG. 4

[56] References Cited

U.S. PATENT DOCUMENTS

| | | | |
|---|---|---|---|
| 3,656,312 | 4/1972 | Streich | 62/28 |
| 3,797,261 | 3/1974 | Juncker et al. | 62/40 |
| 4,158,556 | 6/1979 | Yearout | 62/28 |
| 4,323,380 | 4/1982 | Muller et al. | 62/28 |
| 4,411,677 | 10/1983 | Pervier et al. | 62/40 |

OTHER PUBLICATIONS

Linde Reports on Science and Technology, 15, 1970.

Primary Examiner—Frank Sever
Attorney, Agent, or Firm—Geoffrey L. Chase; E. Eugene Innis; James C. Simmons

[57] ABSTRACT

A process is set forth for the recovery of methane, nitrogen and natural gas liquids ($C_{2+}$) from a natural gas feed stream wherein the recovery can be made at high pressure by the integration of a nitrogen rejection stage including a heat pump driven distillation column and a natural gas liquids stage. Nitrogen can be rejected over a wide range of nitrogen concentration (approximately 1 to about 80%) of the feed stream.

14 Claims, 1 Drawing Figure

NITROGEN REJECTION FROM NATURAL GAS INTEGRATED WITH NGL RECOVERY

TECHNICAL FIELD

The present invention is directed to the recovery of nitrogen and natural gas liquids (NGL) from a methane-containing feed stream, such as natural gas. The invention is particularly directed to the recovery of nitrogen, a methane rich product and natural gas liquids from a methane-containing feed stream wherein the nitrogen level varies in the feed stream. More particularly, the present invention is directed to such a separation wherein the nitrogen and the methane-rich product are maintained at high pressure.

BACKGROUND OF THE PRIOR ART

The production of methane-containing gas streams, such as natural gas, frequently involves the removal of contaminents or components which are not desired in the pipeline product of natural gas production. One such class of components has been referred to as natural gas liquids or NGL. NGL constitutes ethane and higher hydrocarbons which are found in natural gas. Depending upon the current economics and gas dewpoint requirements, it is sometimes desirable to remove the NGL from natural gas. Various distillation methods have been considered for such a separation whereby the cooling of the natural gas accomplishes the separation of the NGL components from the methane components of the natural gas.

An exemplary contaminent which is deemed desirable to remove from natural gas before pipelining is nitrogen. Many production streams of a natural gas include minor but not insignificant levels of nitrogen. In order to meet the specified minimum sales gas heating value or maximum concentration of inert components, this nitrogen is not allowed to remain in the natural gas which is pipelined to market or further transportation. In addition to the naturally occurring levels of nitrogen in some produced natural gas, nitrogen in varying concentrations now occurs in produced natural gas wherein the production of the natural gas associated with oil deposits has been maintained or assisted by nitrogen injection into the strata holding the deposits. Such production techniques are typically referred to as enhanced recovery or non-primary recovery and are more widely utilized as the number of naturally producing natural gas and associated oil deposits decline. Various methods have been utilized for the separation of nitrogen from natural gas. These techniques are typically referred to as nitrogen rejection because the nitrogen is removed as a waste stream or by-product of little or no value, although in some instances recovered nitrogen is reinjected into the strata when it is more economical than the production of fresh nitrogen. The nitrogen rejection is generally effected by the cooling of the nitrogen-containing natural gas and fractionating it in a distillation column.

These procedures for the removal of natural gas liquids or nitrogen usually require the reduction in pressure of the natural gas stream being treated in order to obtain the necessary refrigeration for the separation. Such processes are exemplified by the following prior art.

In U.S. Pat. No. 3,656,312, a process is described wherein a liquefied gas mixture containing methane is separated from ethane and heavier hydrocarbons in a distillation column. The methane recovered in the process is in the liquid state and can be easily pumped to the desired pressure. Separate columns for the separation of ethane from propane, butane and heavier hydrocarbons are contemplated.

U.S. Pat. No. 3,797,261 provides a process for the separtion of natural gas containing nitrogen. The natural gas is separated into a low nitrogen fraction and a high nitrogen fraction. The separation is performed in a distillation column wherein refrigeration is derived from the expansion of the high nitrogen fraction and by the vaporization of a recycle medium in heat exchange relation with the vapor in the column. The high nitrogen fraction, having been expanded to produce necessary refrigeration is removed from the process at atmospheric pressure. The process contemplates a recycle medium which performs additional refrigeration duty for the operation of the column. The methane product is reduced in pressure from approximately 300 psia to 25 psia. This requires the methane product to be recompressed to pipeline pressure of approximately 300 psia. The waste nitrogen from this process is withdrawn from the process at 15 psia or approximately atmospheric pressure. The process requires the reduction in pressure in order to provide the necessary refrigeration for the separation. In the case of natural gas containing greater than 50% nitrogen, the 300 psi feed stream is separated into a nitrogen product which is reduced in pressure to at least 20 psia. The product if desired in liquid form is reduced to 30 psia and if provided in gaseous form is reduced to at least 40 psia. Therefore, in order to recover the variable nitrogen content or the gaseous or liquid methane streams in this process, significant pressure reductions for refrigeration duty are necessary.

U.S. Pat. No. 4,323,380 discloses a process for the separation of nitrogen and ethane from natural gas. The process uses three rectification stages in order to perform the separation. The process is directed to a fixed low content nitrogen feed of natural gas.

Linde Reports on Science and Technology, Vol. 15 (1970) discloses a nitrogen rejection process wherein nitrogen-containing natural gas is introduced into a high pressure column which is operated by a closed circuit methane refrigeration cycle. Again, the process is relevant to a fixed nitrogen content feed gas stream.

The prior art processes generally lack the ability to deliver nitrogen and methane at high pressure in a process which is readily utilizable over a wide range of nitrogen content in the feed. The present invention overcomes these drawbacks as will be more fully described.

BRIEF SUMMARY OF THE INVENTION

The present invention is directed to a process and apparatus for the recovery at high pressure of a substantially pure nitrogen product, an ethane-rich product and a methane-rich product from a methane-containing feed stream, wherein the feed stream has a variable concentration of nitrogen, comprising the steps of cooling a high pressure methane-containing feed stream and separating said stream into an ethane-rich fraction and a nitrogen-rich fraction, introducing said nitrogen-rich fraction into a single, high pressure distillation column, driving said column with a closed loop heat pump refrigerant which condenses an overhead reflux stream, condenses an intermediate reflux stream and vaporizes a reboil stream to said distillation column, removing a high pressure, substantially pure nitrogen product as an overhead stream from said column and rewarming it against the closed loop refrigerant and portions of the feed stream, removing a methane-rich bottom stream from said column, subcooling it in a side reboiler and introducing said stream into a second distillation column as reflux, introducing the ethane-rich fraction into said second distillation column, and removing a methane-rich product from the top of said second column and an ethane-rich product from the bottom of said second column.

The process of the present invention may be utilized on a methane-containing feed stream which has a nitrogen concentration which can vary over a range of approximately 1 to 80% by volume of the feed.

Preferably, the closed loop heat pump refrigerant is divided into a first substream which is expanded to a lower temperature and pressure and a second substream which is condensed against the column reboil stream before being further cooled by said first substream.

It is advantageous in the process of the present invention to utilize at least a portion of the initial feed stream to reboil the second distillation column where natural gas liquids are separated from methane.

Preferably, the ethane-rich fraction of the feed stream which is introduced to the second distillation column is separated from the feed stream in two stages and each separated fraction is introduced individually into the second distillation column for better utilization of refrigeration.

The nitrogen-rich fraction of the initial feed stream can be phase separated, and each phase stream reduced in pressure to produce refrigeration before the individual streams are each introduced into the single high pressure distillation column. Again, this affects a better separation in the column.

DETAILED DESCRIPTION OF THE INVENTION

Figure 1:
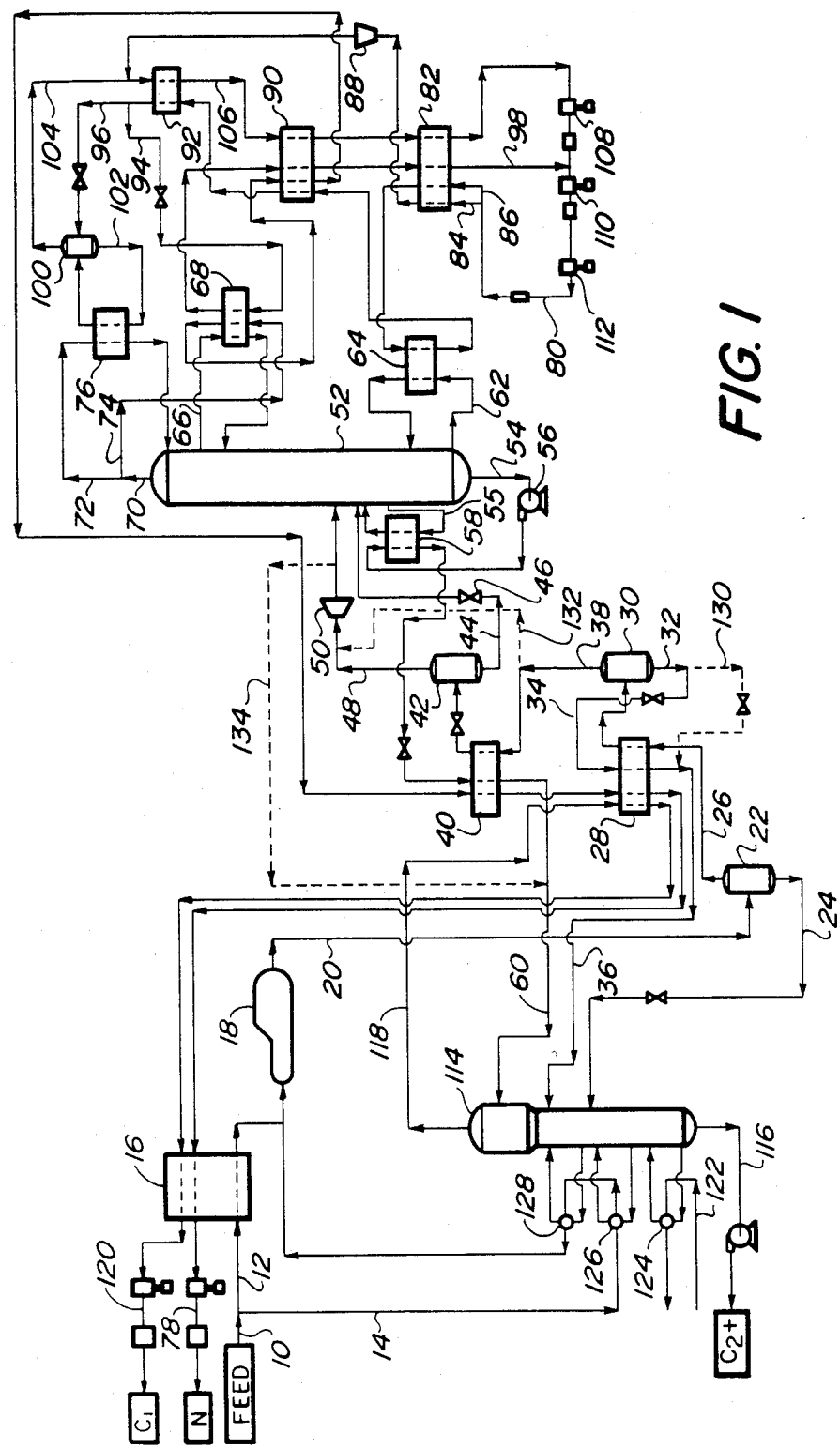
FIG. 1 is a schematic drawing of the flow scheme of the present invention showing the nitrogen rejection stage, the NGL stage and a manner of operation without the nitrogen rejection stage.

The present invention provides an energy efficient mode for the treatment of methane-containing feed streams, such as natural gas, in order to remove nitrogen, which may exist in varying concentrations, as well as natural gas liquids, such as ethane and heavier hydrocarbons. These products are separated and removed at high pressure, which thus avoids the apparatus, such as compressor equipment, and energy, particularly compression power, that would be required if the separation were performed at low pressure or if the necessary refrigeration was derived from pressure reductions in the various streams, generally referred to as autorefrigeration.

This type of separation and recovery of both nitrogen and a methane-rich product is particularly well adapted to natural gas production where the production is dependent upon nitrogen injection into the natural gas producing strata in order to maintain well head pressure. During the initial phases of natural gas recovery with nitrogen pressure maintenance, the nitrogen content of the produced natural gas is fairly low. However, over the lifetime of the natural gas well's production, the nitrogen content of the produced natural gas increases as the amount of natural gas is diminished and the wave front of injected nitrogen breaks through to the well outlet. Therefore, during production, the nitrogen content varies and in fact generally increases, sometimes from a negligible level of nitrogen up to approximately 80% by volume of the feed. In order to successfully and economically operate such a natural gas production, it is necessary to remove nitrogen from the natural gas to meet pipeline specifications for natural gas, as well as to recover the nitrogen for re-injection into the pressure maintenance zone of the producing well. In order to remain economical, the nitrogen recycle or reinjection stream should be available at high pressure without the need for significant recompression. Therefore, it is desirable for a process to remove or reject nitrogen from natural gas without the necessity of significantly dropping the pressure of the recovered nitrogen. The present invention achieves such a goal, along with the successful integration of a natural gas liquids recovery scheme into the nitrogen recovery or nitrogen rejection scheme. The nitrogen content of the natural gas to be processed by the present invention can vary over the range of 1 to about 80%.

Another advantage of operating the nitrogen rejection and NGL recovery at high pressure is that feed gas may contain a higher percentage of carbon dioxide without said carbon dioxide freezing and forming solids to clog the apparatus.

Yet another advantage of the present invention is that both nitrogen product and methane-rich product are removed from the process at similar high pressures. Therefore, the compression capacity of the process equipment can be easily shifted for the varying quantities of nitrogen and methane as the nitrogen concentration in the produced feed stream changes over the life of a producing well which the present invention is used in conjunction therewith. At low nitrogen feed stream concentrations, the final product compression capacity can be used predominantly for methane recompression. At high nitrogen feed stream concentrations, the final product compression capacity can be shifted to be used more for nitrogen product recompression.

High recovery of methane and rejected nitrogen is possible over a wide range of nitrogen concentrations in the feed stream of natural gas to be processed, because the necessary refrigeration duty to operate the nitrogen rejection column is to a large extent available from a closed loop heat pump refrigeration cycle. In order to adjust for the varying conditions under variable nitrogen concentrations, the closed loop heat pump refrigeration cycle is split into two substreams wherein a first substream can be expanded to provide additional refrigeration for refluxing the first distillation column where nitrogen rejection occurs.

The closed loop heat pump refrigeration cycle includes a turbine expander which provides a controlled and variable amount of refrigeration to the nitrogen rejection column. By providing supplemental refrigeration to the column, this expander allows for the removal of a portion of the feed stream from the main flow of the feed stream before it enters the nitrogen rejection column. The removed portion is introduced into the NGL or second column. This removal constitutes a loss of refrigeration to the nitrogen rejection column and requires that refrigeration be provided, such as by the heat pump turbine expander. Therefore, the amount of ethane recovered in the second distillation column can be controlled and adjusted by changing the output of the turbine expander in the heat pump cycle. Also, by making up any refrigeration loss from the nitrogen rejection column caused by the removed portion of the feed stream, the turbine expander utilization avoids the necessity of deriving refrigeration by the reduction in pressure of the methane-rich product, thereby maintaining high pressure in said methane-rich product.

The second distillation column of the process of the present invention for natural gas liquids recovery is at last partly reboiled with a portion of the initial feed stream to the process. This accomplishes an improved separation of the methane components fed to the distillation column from the ethane and heavier hydrocarbons. This distillation column is fed with three separate feed streams, which also contribute to the improved separation. Two of these individual feeds are separated from the initial feed stream as ethane-rich fractions, while the third feed to the second distillation column constitutes the methane-rich bottom stream from the first or nitrogen rejection distillation column.

With reference to FIG. 1, the process of the present invention will be described in greater detail. The process is amenable to various methane-containing feed streams, but for the purposes of description, the feed stream will be referred to as a natural gas stream.

Natural gas containing nitrogen and natural gas liquids is recovered from a well head, then being produced with the assistance of nitrogen injection. The natural gas after bulk $CO_2$ removal is dried and introduced in line 10 at a pressure of approximately 850 psia and 90° F. A sidestream is split out from the main feed stream in line 14. This stream is used to provide a portion of the reboil in the second distillation column 114 which removes natural gas liquids. After passing through reboilers 126 and 128, the stream 14 is returned to the main feed stream. The reboilers are actually located below the bottom feed 24 of column 114, but for purposes of illustration they are shown at a height on the column above where they would actually be. The remaining portion of the main feed stream 12 is cooled against product streams in heat exchanger 16 before being combined with sidestream 14 and further cooled by propane refrigeration in heat exchanger 18. The partially condensed feed stream in line 20 is introduced into a phase separator 22 wherein the liquid phase is removed as a bottom stream in line 24 as a first ethane-rich fraction which is fed to the second or NGL distillation column 114. The vapor phase of the feed stream is removed as an overhead in line 26 and is further cooled in heat exchanger 28. Additional liquid is condensed during this cooling and the stream is introduced into a second phase separator 30. A second ethane-rich fraction is removed from the bottom of a second phase separator 30 in line 32. The ethane-rich fraction is reduced in pressure in line 34 before being rewarmed and partially vaporized in heat exchanger 28 and then introduced in line 36 as an intermediate feed to the second or NGL distillation column 114.

The vapor phase from the second feed separator 30 in line 38 is further cooled against process streams in the main heat exchanger 40. This stream is a nitrogen-rich fraction of the initial feed stream and contains predominently nitrogen and methane. After being cooled in heat exchanger 40, the nitrogen-rich fraction is phase separated in the third phase separator 42. The liquid phase in line 44 is reduced in pressure through valve 46 before being introduced into the first distillation column 52 as the lower of two feeds to this column. The vapor phase from the separator 42 is removed as an overhead stream in line 48 and reduced in pressure by being expanded through a turbine or expander 50 before being introduced into the first distillation column 52 as a second feed supplied to the column at a level above the feed in line 44.

The distillation performed in the first distillation column 52 is designed to separate nitrogen from a predominently methane stream, which is typically referred to as nitrogen rejection. The nitrogen rejection or separation from the methane containing natural gas is performed at high pressure, which in this instance is approximately 300 to 400 psia. Nitrogen is removed as an overhead stream in line 70 while a methane-rich bottom stream is removed from the column 52 in line 54.

The column 52 is reboiled by removing a portion of the bottom fraction in line 62 and rewarming it in heat exchanger 64 against a closed loop heat pumped refrigerant. Additional reboil is provided by removing a stream 55 above the reboil stream 62 in column 52 and heat exchanging it against the methane-rich bottom stream in line 54 in side reboiling heat exchanger 58 before re-introducing the reboil into the column 52.

The column 52 is refluxed by splitting out a portion of the substantially pure nitrogen product from line 70 in line 72 and totally condensing this stream in a condensing heat exchanger 76 before returning the nitrogen as reflux to the overhead of the column 52. The condensing heat exchanger 76 is supplied with cold refrigerant from the closed loop, heat pumped refrigeration cycle which also flows through reboil heat exchanger 64. The remaining portion of stream 70 is removed as a substantially pure nitrogen product of the nitrogen rejection column 52 in line 74. The product in line 74 is rewarmed in a side condensing heat exchanger 68, which along with the refrigerant from the closed loop, heat pump refrigeration cycle cools an intermediate side reflux stream in line 66. The intermediate reflux stream in line 66 improves the energy efficiency of the separation of the nitrogen and methane fractions in the first distillation column 52.

The substantially pure nitrogen product in line 74 emanating from heat exchanger 68 is then further rewarmed in heat exchanger 90 against a subcooled high pressure stream of the closed loop heat pump refrigeration cycle. The nitrogen product in line 74 is further warmed in the main heat exchanger 40 and the heat exchanger 28 against a portion or fraction of the feed gas stream. Finally, the nitrogen is rewarmed in heat exchanger 16 against the remaining portion of the feed stream in line 12 before being removed as a nitrogen product in line 78. The nitrogen can be compressed and reutilized for nitrogen injection in an injection well associated with a producing well for natural gas. The nitrogen is removed from the process of the present invention at a pressure of approximately 300 to 400 psia. This high pressure gas is then further compressed for enhanced recovery utilization as described above.

The first distillation column 52 which performs the separation or rejection of nitrogen from the methane fraction of the feed gas stream is driven by a closed loop, heat pump refrigeration cycle. The refrigerant utilized in the cycle is methane, although other refrigerants may be utilized particularly depending upon the feed stream processed, as well as mixed refrigerants. The refrigerant in line 80 which has been compressed to approximately 365 psia is split into a first substream in line 84 and a second substream in line 86. The first substream 84 is cooled in the main heat exchanger 83 for the refrigeration cycle and then is reduced in pressure through expansion turbine or expander 88 to provide at least a portion of the refrigeration to reflux the column. This refrigerant is combined with refrigerant which has seen duty in condensing the overhead reflux stream of the distillation column 52, such refrigerant being returned in line 104 and the combined streams in line 104 and 84 are used to cool refrigerant in cold heat exchanger 92. The second substream in line 86 is also cooled in the main heat exchanger 82 before being further cooled and condensed in reboiling heat exchanger 64 against reboil in line 62 for the column 52. The refrigerant in line 86 is subcooled in heat exchanger 90 against refrigerant streams and the nitrogen product stream before being further subcooled in cold heat exchanger 92 against returning refrigerant in line 104 and the expanded refrigerant in substream 84. The second substream now in line 96 is reduced in pressure and phase separated in phase separator 100. The liquid phase in line 102 is used to condense a nitrogen reflux 72 to the column 52 by way of the condensing heat exchanger 76. The evaporated refrigerant in line 102 is returned to the separator vessel 100. The vapor phase of the refrigerant in the separator vessel 100 is removed in line 104 and combined with the first substream 84 from the expansion turbine 88. The combined refrigerant is rewarmed in the cold heat exchanger 92 and is removed in line 106 before being further rewarmed in heat exchangers 90 and 82 against refrigerant streams. This refrigerant has been expanded and reduced in pressure in order to provide the coldest (lowest) level of refrigeration duty for the column and therefore requires an additional stage of recompression before recycle. This initial stage of recompression is performed in compressor 108.

A sidestream 94 is split out of the second substream in line 86 after the substream 86 is cooled in cold heat exchanger 92. The split out refrigerant stream in line 94 provides refrigeration duty for the intermediate reflux stream line 66 by supplying a portion of the cooling necessary in the heat exchanger 68. The stream is then rewarmed and returned through heat exchangers 90 and 82 and enters the recompression portion of the refrigeration cycle in line 98. This refrigerant in line 98 is at an intermediate pressure level and is combined with the partially recompressed refrigerant emanating from compressor 108. The combined warm refrigerant is further recompressed in compressors 110 and 112 before being returned to refrigeration duty. The refrigerant is aftercooled in a heat exchanger downstream of each compressor.

The methane-rich bottom stream 54 removed from the base of the first distillation column 52 is then transferred to the second distillation column 114 by pump 56. The stream first passes through side reboiling heat exchanger 58 to provide an additional increment of reboil to the first column, and is then reduced in pressure prior to entering heat exchanger 40. The stream is then rewarmed in the main heat exchanger 40 before being introduced into the second distillation column 114 as the uppermost feed to said column in line 60. The second distillation column which is utilized to separate a methane-rich product from NGL components such as ethane, propane, butane and other heavy hydrocarbons is supplied with three distinct feeds in lines 24, 36 and 60. This provides improved separation within the column because each stream has undergone at least some preliminary separation before being introduced as a lower, intermediate and an upper feed stream to the column 114, respectively. In addition to the three distinct feeds to the second distillation column 114, the separation of NGL products from the methane-rich product is also accomplished with the aid of a series of three reboilers 124, 126 and 128. The lowest reboiler is operated by heat exchange against an external heating source in line 122 through exchanger 124. The second and third reboilers are operated by heat exchange of the sidestream 14 of the initial feed stream which is passed through heat exchangers 126 and 128. Reboiler 128 would actually be located below feed 24, but for clarity is shown higher in FIG. 1. The three side reboilers provide sufficient vapor phase within the distillatin column to effectively remove most of the methane from the natural gas liquids which descend the column and are removed in line 116 as an ethane-rich product. The methane-rich product in line 118 is removed as an overhead fraction from the column 114 and is rewarmed against the feed stream in heat exchanger 28 and 16. The methane is recovered at approximately 300 psia and is approximately 90% pure methane. The methane-rich product can be recompressed to pipeline pressure.

A specific example of the process of the present invention is set forth herein for a natural gas feed stream containing approximately 50% nitrogen by volume. A feed stream is introduced into line 10 at approximately 850 psia and 90° F. The stream is approximately 54% nitrogen, 35.5% methane, 6% ethane, 2.6% propane, 1.5% butane and higher hydrocarbons as well as residual components such as carbon dioxide and aromatics. From this feed, two ethane-rich fractions are separated for introduction into the NGL column while a feed in line 38 is directed to the nitrogen rejection column 52. This stream is at approximately 800 psia and −163° F. It constitutes 92% of the initial feed stream and contains 58% nitrogen, 36.7% methane, 4.4% ethane, 0.7% propane and the remainder of the residuals described above. The substantially pure nitrogen product recovered from the distillation column in line 74 is at a pressure of approximately 340 psia and −245° F. When finally removed in line 78 but before recompression, the stream is at approximately 324 psia and 80° F. This stream constitutes 52% of the initial feed and 56% of the feed to the nitrogen rejection distillation column. The stream contains 99.3% nitrogen and 0.7% methane. The methane-rich bottom stream from the distillation column 52 in line 54 is at approximately 345 psia and −156° F. It constitutes 39% of the initial feed stream and 43% of the feed to the nitrogen rejection distillation column 52. It has a composition of 4% nitrogen, 84% methane, 10% ethane, 1.6% propane, with the residuals of butane and higher hydrocarbons constituting the remainder of the composition. This stream becomes the uppermost feed to the second distillation column for the separation of NGL. The stream constitutes 83% of the feed to this distillation column 114. The two ethane-rich fractions which are separated from the initial feed stream each constitutes 4% of the initial feed. The intermediate ethane-rich fraction which is fed to the second distillation column 114 which is supplied in line 36 constitutes 8.3% of the total feed to the second distillation column and has a composition of 10% nitrogen, 27.5% methane, 62.2% ethane and higher hydrocarbons plus other residuals. The lowermost ethane-rich fraction which is fed to the second distillation column 114 in line 24 constitutes 8.5% of the feed to said column and is comprised of 6.7% nitrogen, 18% methane and 71.7% ethane and higher hydrocarbons plus residuals. The methane-rich product removed from the column 114 in line 118 is at approximately 300 psia and −129° F. as it leaves the column and exits the process at approximately 285 psia and 80° F. before recompression. This methane-rich product constitutes 39% of the initial feed stream and 81% of the feed to the NGL stage of the process. The composition of the stream is 6% nitrogen, 90.8% methane and 3.2% ethane plus hydrocarbons. The ethane-rich product removed from the second distillation column 114 in line 116 is at a pressure of approximately 315 psia and 72° F. It constitutes 9% of the initial feed stream and 19% of the feed to the NGL stage of the overall process. This ethane-rich product comprises negligible amounts of nitrogen, 0.4% methane, 53% ethane, 29% propane, 16% butane and higher hydrocarbons as well as some residuals comprising carbon dioxide and aromatics. Compositions of the various process streams of the process will change as the composition of the feed stream changes, particularly the composition with respect to the varying concentrations of nitrogen in a nitrogen enhanced recovery of the natural gas well.

The present invention incorporates a unique integration of a nitrogen rejection column and a natural gas liquids recovery column. The integration includes three unique process steps; the reflux of the second column (NGL) with the methane-rich bottom stream of the nitrogen rejection column, the refrigeration of the nitrogen rejection column with the turbine expander of the heat pump cycle which allows removal of ethane-rich portions from the feed stream, and the partial vaporization of the second ethane-rich stream against the feed stream to provide additional refrigeration to the feed stream.

The present invention in the preferred embodiment provides a unique integrated natural gas liquids recovery with nitrogen rejection which is operable over a wide range of nitrogen concentrations in the feed gas. This is possible because of the integration of process streams and because of the use of a closed loop heat pumped refrigeration cycle to drive the nitrogen rejection stage of the process in the first distillation column 52. However, under some circumstances of low nitrogen content feeds, it may not be desirable to process the feed stream through the nitrogen rejection stage of the process because of the low volume of nitrogen recoverable and because extremely low nitrogen content in the untreated feed stream will meet pipeline specifications for natural gas. However, it may still be desirable to remove natural gas liquids from such low nitrogen-containing natural gas feed streams. In that event, the nitrogen rejection stage of the process may be disconnected from the natural gas liquids recovery stage of the process as illustrated in FIG. 1 by the dotted lines 130, 132 and 134. Although the appropriate valving is not illustrated, when nitrogen rejection is not desired, the second ethane-rich fraction in line 32 can be diverted around heat exchanger 28 by passing the stream through line 130 and sending it directly to the second distillation column 114. The nitrogen-rich fraction in line 38 which contains the predominent amount of methane and the insignificant level of nitrogen contained in the initial feed stream can be diverted through line 132 and feed expansion turbine 50 before being diverted from the nitrogen rejection stage and distillation column 52 by appropriate valving which directs the nitrogen-rich fraction through line 134 and line 60 directly to the NGL stage in the distillation column 114. This sequence would only be used when the nitrogen content of the initial feed stream is not required to be separated from the methane-rich product.

The present invention as described in the former preferred embodiment provides an energy efficient method for the separation and recovery of a high purity high pressure methane-rich product, a high purity high pressure nitrogen product and an ethane-rich product which is typically referred to as natural gas liquids and which may contain other hydrocarbons in addition to ethane such as propane and butane. The process is amenable to such a separation over a wide range of nitrogen concentration in the methane-containing feed stream.

Although the present invention has been described with reference to a preferred embodiment, it is believed that various obvious modifications can be made in the invention without departing from the scope of the invention which should be ascertained from the claims which follow.

We claim:

1. A process for the recovery at high pressure of a substantially pure nitrogen product, an ethane-rich product and a methane-rich product from a methane-containing feed stream wherein the feed stream has a variable concentration of nitrogen comprising:
   (a) cooling a high pressure methane-containing feed stream comprising a variable nitrogen concentration of approximately 1 to 80 volume percent and separating said stream into an ethane-rich fraction and a nitrogen-rich fraction;
   (b) heat exchanging the nitrogen-rich fraction against a methane-rich stream wherein both streams are at relatively high pressure and reducing the nitrogen-rich fraction in pressure at least in part through an expander before introducing said nitrogen-rich fraction into a first high pressure distillation column;
   (c) driving said column with a closed loop heat pump refrigerant which condenses an overhead reflux stream, condenses an intermediate reflux stream and vaporizes a reboil stream to said distillation column wherein a portion of the refrigeration for the reflux of the column is produced by expanding the refrigerant through an expansion turbine;
   (d) removing a high pressure, substantially pure nitrogen product as an overhead stream from said column and rewarming it against the closed loop refrigerant and portions of the feed stream;
   (e) removing a methane-rich bottom stream from said column and introducing said stream into a second distillation column as reflux to recover additional hydrocarbon;
   (f) introducing the ethane-rich fraction of step (a) into said second distillation column; and
   (g) removing a methane-rich product at high pressure from the top of said second column and an ethane-rich product from the bottom of said second column.

2. The process of claim 1 wherein the closed loop heat pump refrigerant is divided into a first sub-stream which is expanded to a lower temperature and pressure and a second sub-stream which is condensed against the column reboil stream before being subcooled by said first substream.

3. The process of claim 1 wherein at least a portion of the feed stream is used to reboil the second distillation column.

4. The process of claim 3 wherein the second distillation column is also reboiled with an external source of propane.

5. The process of claim 1 wherein the ethane-rich fraction is separated in two stages from the feed stream and each separated fraction is introduced individually to the second distillation column.

6. The process of claim 5 wherein the two stage separation provides a first and a second ethane-rich fraction and said second fraction is partially vaporized against the feed stream.

7. The process of claim 1 wherein the nitrogen-rich fraction is split and reduced in pressure before introduction into the first high pressure distillation column.

8. The process of claim 1 wherein the methane-rich bottom stream reboils the first high pressure distillation column by heat exchange in a side reboiler while being subcooled.

9. The process of claim 1 wherein the substantially pure nitrogen rich product condenses, at least in part, a side reflux stream to the first high pressure distillation column.

10. The process of claim 1 wherein the nitrogen-rich fraction to the first distillation column is first expanded to an intermediate high pressure through an expander before being heat exchanged against a methane-rich stream.

11. An apparatus comprising elements designed, sized and arranged for the recovery at high pressure of a substantially pure nitrogen prodct, an ethane-rich product and a methane-rich product from a methane-containing feed stream wherein the feed stream has a variable concentration of approximately 1 to 80 volume percent nitrogen, including:

(a) heat exchange means for cooling said feed stream in order to partially condense the stream and to rewarm a methane-rich stream at high pressure;

(b) phase separator means for separating an ethane-rich liquid phase fraction from a nitrogen-rich vapor phase fraction;

(c) an expander for reducing the pressure and temperature on at least a portion of the nitrogen-rich fraction;

(d) a first distillation column operated at high pressure for the separation of a substantially pure nitrogen product as an overhead stream and a methane-rich bottom stream;

(e) a closed loop heat pump refrigeration cycle which drives the first distillation column, including an expansion turbine wherein a portion of the refrigeration for the reflux of said column is supplied;

(f) a second distillation column for the separation of the ethane-rich fraction of clause (b) and the methane rich bottom stream of clause (d) into a methane-rich product and an ethane-rich product.

12. The apparatus of claim 11 wherein reboiling means are provided for the second distillation column at least a portion of which reboiling means is driven by a portion of the feed stream.

13. The apparatus of claim 11 wherein the heat exchange means comprises a series of heat exchangers which in at least a portion of said exchangers, the feed stream is cooled against process streams.

14. The apparatus of claim 11 in which the closed loop heat pump refrigeration cycle includes heat exchange means for providing reboil, intermediate reflux and overhead reflux to the first distillation column.

* * * * *